United States Patent [19]
Major

[11] Patent Number: 5,865,803
[45] Date of Patent: Feb. 2, 1999

[54] SYRINGE DEVICE HAVING A VENTED PISTON

[76] Inventor: Miklos Major, 1959 Watch Hill Rd., Ambridge, Pa. 15003

[21] Appl. No.: 858,432

[22] Filed: May 19, 1997

[51] Int. Cl.[6] .............................. A61M 1/00; A61M 5/315
[52] U.S. Cl. ........................... 604/122; 604/190; 604/222
[58] Field of Search .................................... 604/181, 187, 604/218, 190, 221, 222, 225, 227, 228, 229, 122, 236

[56] References Cited

U.S. PATENT DOCUMENTS

| | | | |
|---|---|---|---|
| 3,672,369 | 6/1972 | Brown | 604/222 |
| 4,030,498 | 6/1977 | Tompkins | 604/222 |
| 4,632,672 | 12/1986 | Kvitrud | 604/222 |
| 4,846,801 | 7/1989 | Okuda et al. | 604/263 |
| 5,125,898 | 6/1992 | Kaufhold, Jr. et al. | 604/195 |
| 5,238,003 | 8/1993 | Baidwan et al. | 604/190 |
| 5,318,536 | 6/1994 | Williams | 604/195 |
| 5,489,266 | 2/1996 | Grimard | 604/218 |

Primary Examiner—Ronald Stright
Attorney, Agent, or Firm—LaMorte & Associates

[57] ABSTRACT

A syringe assembly specifically designed to dispense high viscosity material. The syringe assembly includes a syringe barrel into which the high viscosity material is placed. A piston assembly is introduced into the syringe barrel. The piston assembly creates a seal against the interior of the syringe barrel that is impervious to the high viscosity material but is not impervious to the passage of air. Consequently, as the piston assembly is advanced into the syringe barrel, any trapped air is permitted to exit the syringe barrel without passing through the high viscosity material. The piston assembly also contains a shaped piston head that stresses the high viscosity material as it is displaced through the syringe barrel. By stressing the high viscosity material in the syringe barrel before it is dispensed, air bubbles and gaps contained within the material can be greatly reduced. Consequently, as the high viscosity material is dispensed from the syringe assembly, a homogenous mix is produced that contains very few air bubbles and gaps.

14 Claims, 5 Drawing Sheets

SYRINGE DEVICE HAVING A VENTED PISTON

BACKGROUND OF THE INVENTION

1. Field of the Invention

The present invention relates to syringes of the type having a syringe barrel and a piston assembly that travels within the syringe barrel, whereby the advancement of the piston assembly in the syringe barrel displaces material from within the syringe barrel and causes that material to be dispensed.

2. Description of the Prior Art

Syringes are used in a wide variety of applications. As a result, the prior art is replete with a large variety of syringe configurations. Hand held syringes are primarily used for dispensing material in a controlled and confined manner. Common uses of syringes include dispensing medications through a needle, dispensing equal parts of epoxy glue onto a surface and dispensing narrow lines of frosting onto a cake. Typically, most prior art syringes function in the same manner regardless to the material they are used to dispense. A prior art syringe typically has a syringe barrel into which the material to be dispensed is held. A piston assembly is positioned at one end of the syringe barrel. The piston assembly is advanced into the syringe barrel by the application of a manual force. As the piston assembly advances within the syringe barrel, the material within the syringe barrel is displaced. This causes the material to be dispensed from a dispensing port present at the far end of the syringe barrel.

To ensure that material within a syringe barrel does not leak past the advancing piston assembly, the piston assembly typically is designed to seal against the interior of the syringe barrel. A common design for a piston assembly is to make a piston head from an elastomeric material in a shape that is slightly wider at points than is the interior of the syringe barrel. When the piston head is placed within the syringe barrel, the oversized sections of the piston head are compressed and seal against the syringe barrel. The seal created by the piston head is typically both air and fluid impervious.

There are two primary ways to fill a syringe barrel with the material that will be eventually dispensed. For low viscosity material, such as water based medical solutions, the material can be drawn into the syringe barrel by retreating the piston assembly in the syringe barrel and creating a negative pressure in the syringe barrel. However, for higher viscosity materials that do not flow under the force of their own weight, such as epoxy, silicone and similar materials, the creation of a negative pressure in the syringe barrel is insufficient to draw the material into the syringe barrel. Rather, for higher viscosity materials, the piston assembly must be removed. The high viscosity material is then filled into the syringe barrel through the piston port. Once filled with a desired amount of high viscosity material, the piston assembly is reintroduced into the syringe barrel, wherein the piston assembly is used to displace the material through the syringe barrel and out the dispensing port.

As material is filled into a syringe barrel, the material becomes mixed with air. Do to the high viscosity of the material, the air may become entrapped within the material. Furthermore, as the piston assembly is reintroduced into the syringe barrel, the air becomes trapped within the syringe barrel in between the piston assembly and the material to be dispensed. As the high viscosity material is displaced through the dispensing port of the syringe barrel, the material mixes with the trapped air. As a result, the material exiting the syringe barrel may contain numerous air bubbles and gaps caused by larger pockets of air.

One specific application that uses a syringe filled with a high viscosity material is in the field of earpiece modeling. In the process of earpiece modeling, a highly viscous impression material is injected onto the opening of the ear using a syringe. The material is allowed to cure in the ear and is then removed. Once removed, the cured impression material can be used to create a hearing aid ear piece of the appropriate size and shape. A problem that occurs in the prior art is that if air becomes entrapped in the impression material while inside the syringe barrel, then the air may cause bubbles and gaps in the final impression that require that the ear impression either be reformed or repaired prior to its use in making a hearing aid.

A need therefore exists in the art for a syringe device that is capable of dispensing a highly viscous material without having air becoming entrapped within the viscous material. Such a need is satisfied by the present invention as described and claimed below.

SUMMARY OF THE INVENTION

The present invention is a syringe assembly specifically designed to dispense high viscosity material. The syringe assembly includes a syringe barrel into which the high viscosity material is placed. A piston assembly is introduced into the syringe barrel. The piston assembly creates a seal against the interior of the syringe barrel that is impervious to the high viscosity material but is not impervious to the passage of air. Consequently, as the piston assembly is advanced into the syringe barrel, any trapped air is permitted to exit the syringe barrel without passing through the high viscosity material.

The piston assembly contains a shaped piston head that stresses the high viscosity material as it is displaced through the syringe barrel. By stressing the high viscosity material in the syringe barrel before it is dispensed, air bubbles and gaps contained within the material can be greatly reduced. Consequently, as the high viscosity material is dispensed from the syringe assembly, a homogenous mix is produced that contains very few air bubbles and gaps.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Figure 1:
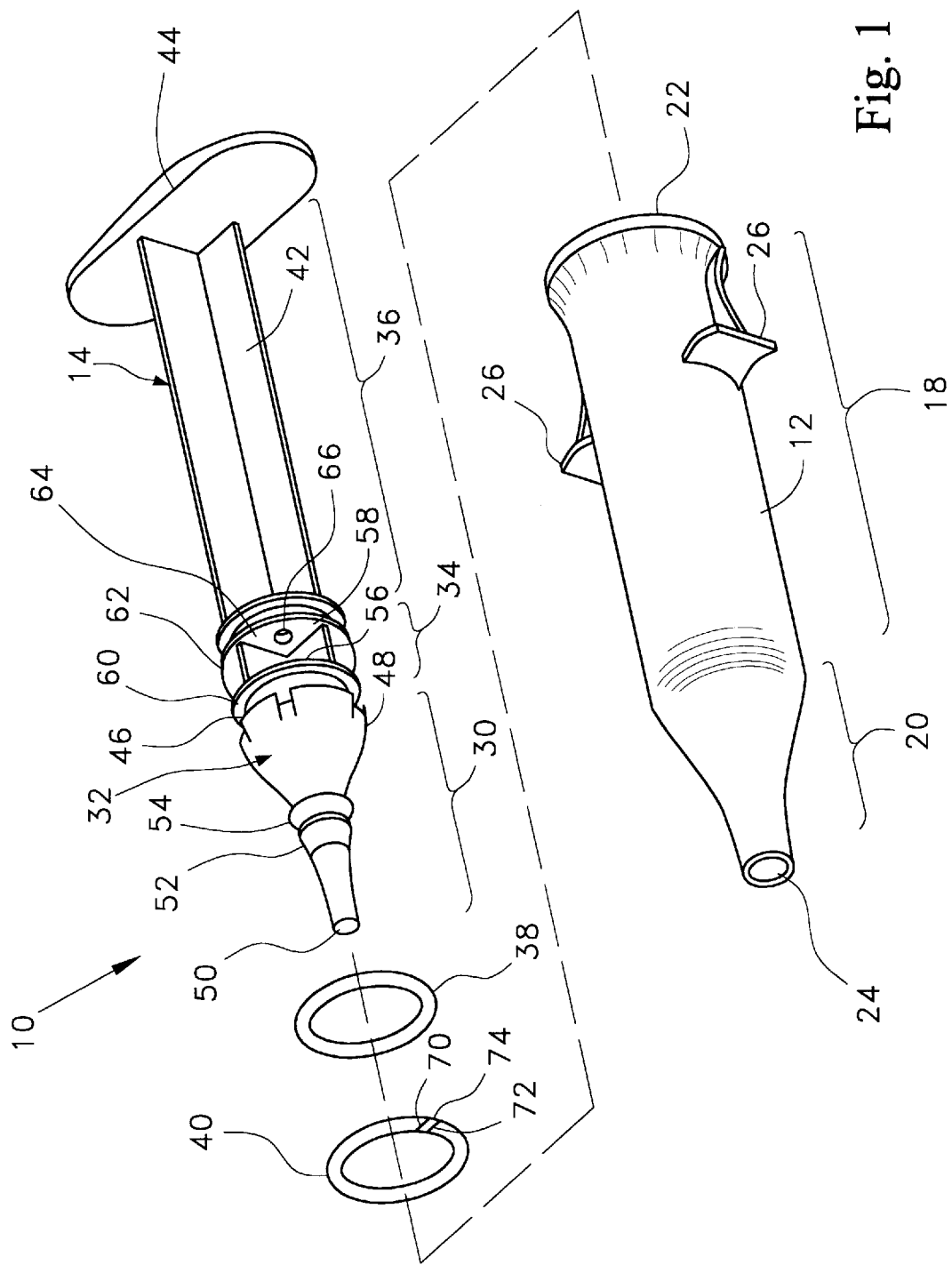
FIG. 1 is an exploded perspective view of one preferred embodiment of the present invention syringe device.
Figure 2:
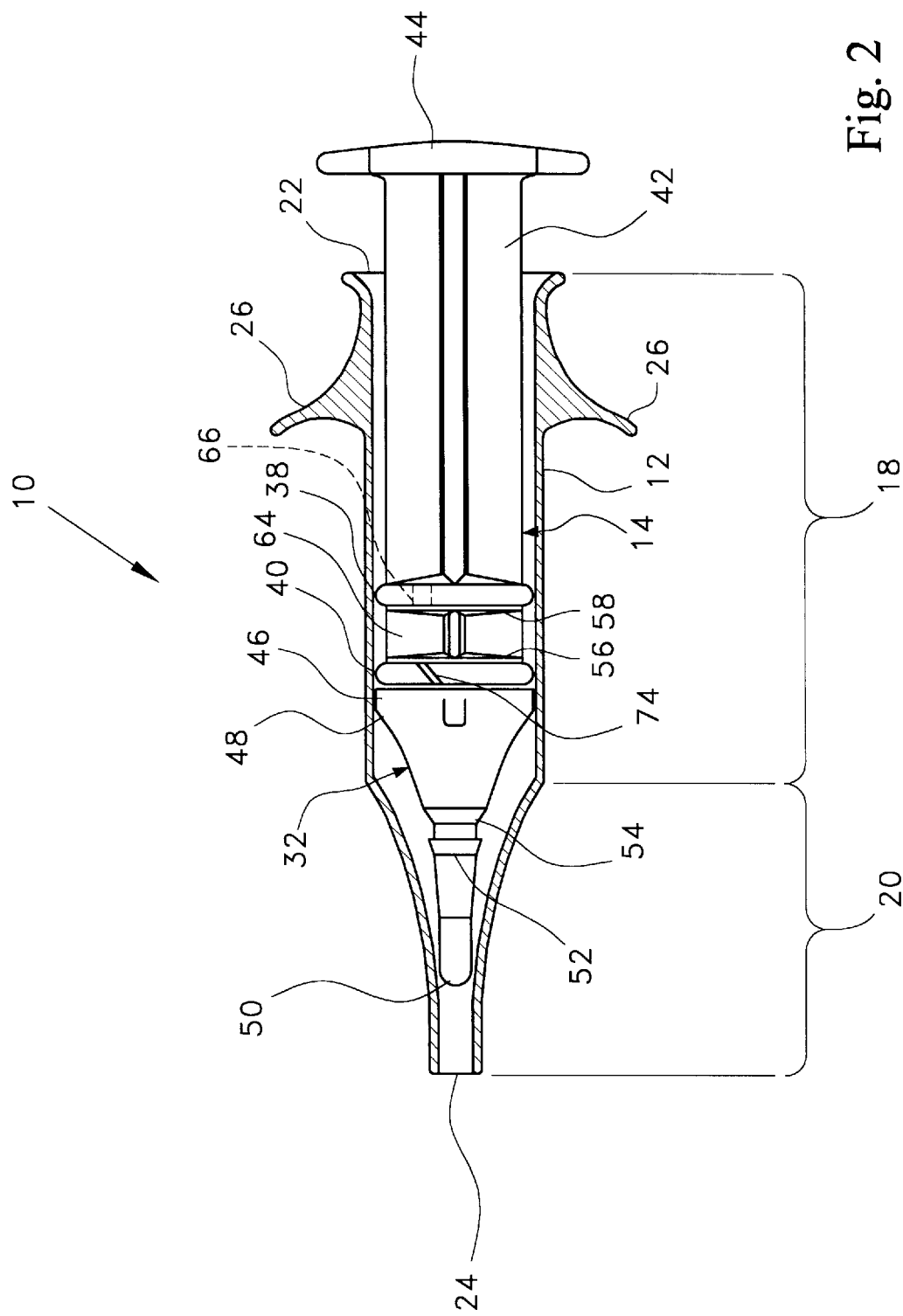
FIG. 2 is a side view of the syringe device shown in FIG. 1 with the syringe barrel shown in cross-section to expose the elements of the piston assembly contained therein.

Referring to FIG. 1 and FIG. 2, a first embodiment of the present invention syringe device 10 is shown. The syringe device 10 contains a syringe barrel 12 and a piston assembly 14 that moves reciprocally within the confines of the syringe barrel 12.

The syringe barrel 12 is a tubular structure containing a cylindrical body region 18 and a tapered neck region 20. The distal end 22 of the cylindrical body region 18 is opened, thereby enabling access into the interior of the syringe barrel 12 by the piston assembly 14. In the shown embodiment, the distal end 22 of the cylindrical body region 18 is slightly flared. The flared open distal end 22 makes it easier to introduce material into the interior syringe barrel 12. The flared open distal end 22 also facilitates the introduction of the piston assembly 14 into the syringe barrel 12, as will later be explained.

The tapered neck region 20 of the syringe barrel 12 tapers down to a small open dispensing port 24 at the front of the syringe barrel 12. The dispensing port 24 can have any configuration known in the prior art and can be configured to attach to a needle, dispensing tube or any other secondary dispensing tip. In the shown embodiment, no secondary dispensing tip is required. As a result, the open dispensing port 24 is smooth and does not contain threads or another configuration that would enable the dispensing port 24 to attach to a secondary dispensing tip.

Flanges 26 radially extend from the exterior of the syringe barrel 12 at points proximate the distal end 22 of the cylindrical region 18. The purpose of the flanges 26 is to provide a point where two fingers can engage the syringe barrel 12, thereby enabling a manual force to be applied to the syringe barrel 12 that biases the syringe barrel 12 against the piston assembly 14. In the prior art, there are many different configurations for flanges on the exterior of a syringe barrel. Any such flange configuration can be adapted for use with the present invention.

The piston assembly 14 of the present invention is divided into three sections 30, 34, 36 (FIG. 1). The first section 30 contains the displacement head 32. As will be later explained, one of the purposes of the displacement head 32 is to displace material out of the tapered region 20 of the syringe barrel. The second region 34 (FIG. 1) of the piston assembly 30 contains two O-ring seals 38, 40 that create a seal in between the piston assembly 14 and the syringe barrel 12. The third section 36 (FIG. 1) of the piston assembly 14 contains the ramrod 42 that advances the piston assembly 14 and the thumb plate 44 that enables a manual force to be comfortably applied to the ramrod 42.

The displacement head 32 has a base 46 that has a diameter that is only slightly smaller than the interior diameter of the cylindrical region 18 of the syringe barrel 12. Four stop blocks 48 extent slightly forward from the base 46 of the displacement head 32. The four stop blocks 48 abut against the interior of the tapered region 20 of the syringe barrel 12 when the piston assembly 14 is fully advanced into the syringe barrel 12. The abutment of the stop blocks 48 against the interior of the syringe barrel 20 prevents the piston assembly 14 from being overly advanced within the syringe barrel 12. This prevents the piston assembly 14 from becoming wedged within the syringe barrel 12 and prevents the piston assembly 14 from cracking the syringe barrel 12 so that it can be repeatedly reused.

The displacement head 32 tapers to a blunt point 50 from the base 46. The slope of the taper between the wide base 46 and the blunt point 50 is approximately equivalent to that of the interior of the tapered region 20 of the syringe barrel 12. As such, when the displacement head 32 is fully advanced into the tapered region 20 of the syringe barrel 12, the displacement head 32 nearly completely fills the volume defined by interior the tapered region 20. Near the center of the displacement head 32 are located two minor diversion flanges 52, 54. As will later be more fully explained, the purposes of these diversion flanges 52, 54 is to direct material toward the interior wall of the tapered region 20 of the syringe barrel 12 and to help displace that material out the open dispensing port 24 at the tip of the syringe barrel 12.

The second region 34 (FIG. 1) of the piston assembly 14 contains two circular flanges 56, 58. The peripheral edge of each of the circular flanges 56, 58 contains a semi-circular groove 60, 62 (FIG. 1) for receiving an O-ring. The two circular flanges 56, 58 are disposed in parallel planes and are concentrically aligned along the same axis a predetermined distance apart. As a result, a baffle chamber 64 is created in the second region 34 (FIG. 1) of the piston assembly 14 in between the two circular structures 56, 58. The forward circular flange 56 is solid and is both air and fluid impervious. The rearward circular flange 58 is not solid. Rather, at least one aperture 66 is formed through the structure of the rearward circular flange 58. As a result, air can freely flow through the rearward circular flange 58 both in and out of the baffle chamber 64.

The rearward O-ring 38 that sits in the semi-circular groove around the rearward circular flange 58 is a solid O-ring having an outside diameter that is slightly larger than the interior diameter of the cylindrical region 18 of the syringe barrel 12. As a result, when the rearward O-ring 38 passes into the syringe barrel 18 a slight interference fit is created and the rearward O-ring 38 creates an air impervious seal with the interior of the syringe barrel 12.

The forward O-ring 40 that sits in the semi-circular groove around the forward circular flange 56 is not a solid O-ring. Rather, the forward O-ring 40 is split so that the O-ring has a first end 70 (FIG. 1) and a second end 72 (FIG. 1) and a gap 74 is disposed in between the first end and the second end of the O-ring. The forward O-ring 40 has a diameter that is generally equivalent to that of the rearward O-ring 38. As the forward O-ring 40 passes into the syringe barrel 12, the O-ring 40 is compressed and the gap 74 in between the first end 70 (FIG. 1) and the second end 72 (FIG. 1) of the O-ring 40 narrows. The narrowed gap 74 is small enough to inhibit the flow of high viscosity material through the gap 74. However, the gap 74 is large enough to allow for the passage of air through the gap 74. Consequently, as the piston assembly 14 is advance into the syringe barrel 12, air is able to pass into the baffle chamber 64 through the gap 74 in the forward O-ring 40. The air in the baffle chamber 64 is then allowed to pass out of the syringe barrel 18 through the aperture 66 or apertures below the rearward O-ring 38.

Figure 3:
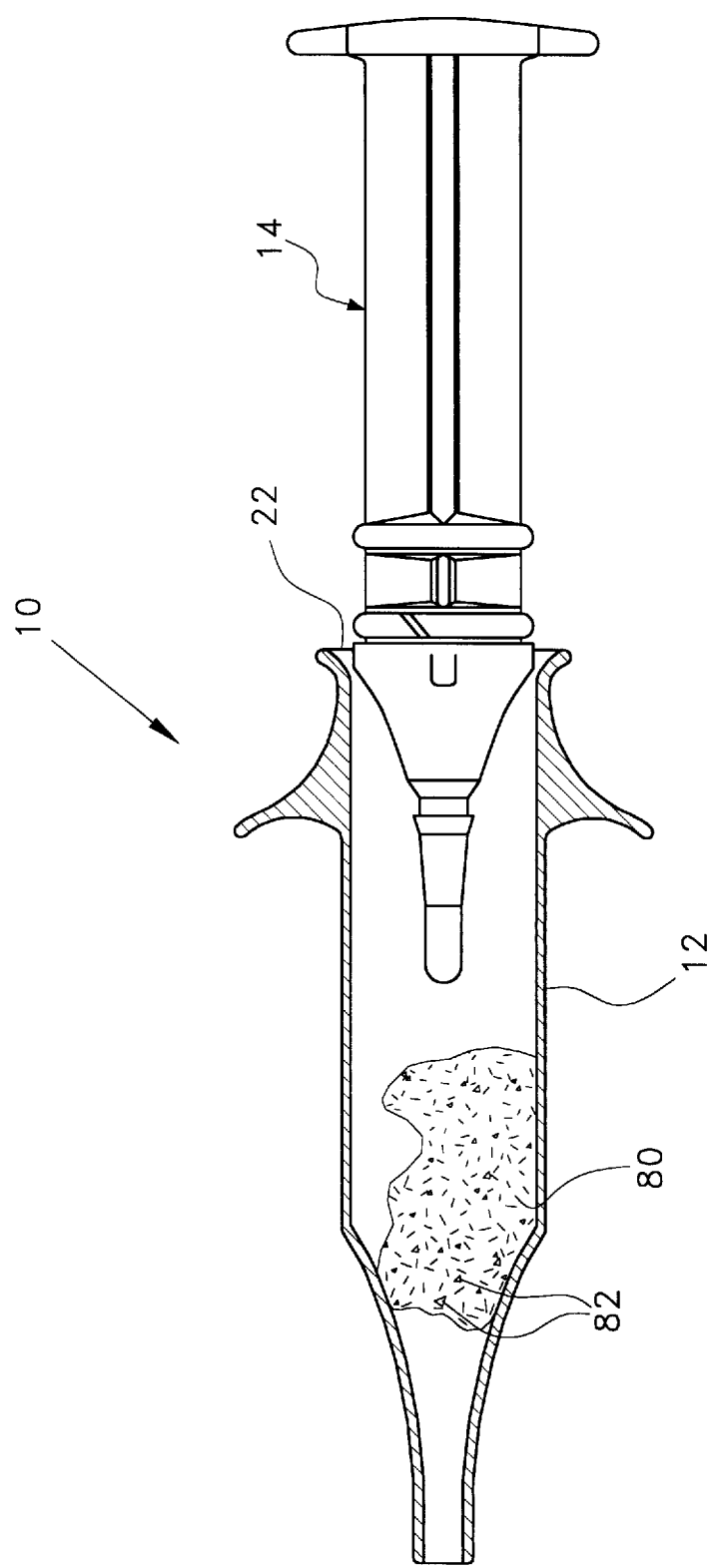
FIG. 3 is a side view of the syringe device shown in FIG. 2 at a point in time where a material to be dispensed is first introduced into the syringe barrel.

Referring to FIG. 3, the use and function of the syringe device 10 can be initially described. To use the syringe assembly 10, the piston assembly 14 is removed from the syringe barrel 12 and a predetermined volume of a high viscosity material 80, such as silicon impression material, is placed within the syringe barrel 12 through the open distal end 22 of the syringe barrel 12. As the high viscosity material 80 is placed within the syringe barrel 12, it may have air pockets 82 trapped within the material. Once the high viscosity material 80 is in place, the piston assembly 14 is reintroduced into the open distal end 22 of the syringe barrel 12.

Figure 4:
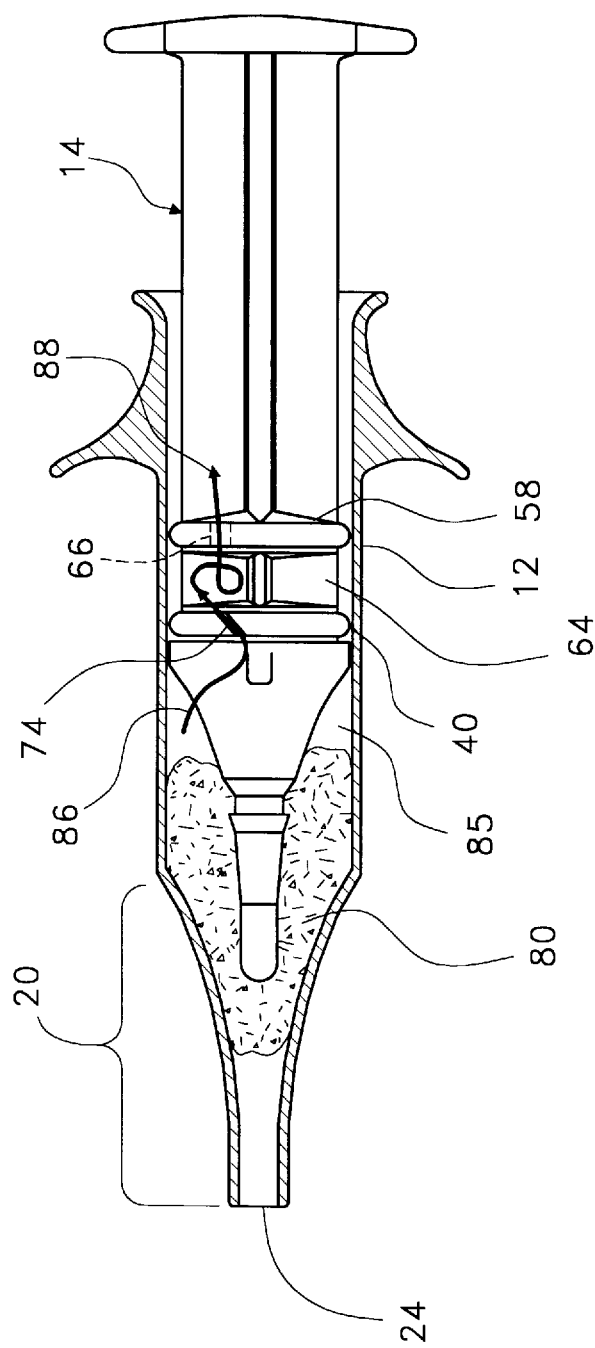
FIG. 4 is a side view of the syringe device shown in FIG. 2 at a point in time where the material in the syringe barrel is first displaced by an advancing piston assembly.

Referring to FIG. 4, it can be seen that as the piston assembly 14 is advanced toward the high viscosity material 80, the high viscosity material 80 moves into the tapered region 20 of the syringe barrel 12 and blocks the dispensing port 24. Once the dispensing port 24 is blocked, the air 85 trapped in front of the advancing piston assembly 14 cannot be displaced through the forward dispensing port 24. As the piston assembly 14 is advanced, the pressure of the trapped air 85 rises slightly and that air flows through the gap 74 of the forward O-ring 40 and into the baffle chamber 64, as is indicated by arrow 86. As the air pressure within the baffle chamber 64 increases, the air flows out of the syringe device 10 through the aperture 66 or apertures in the rearward circular flange 58, as is indicated by arrow 88.

Figure 5:
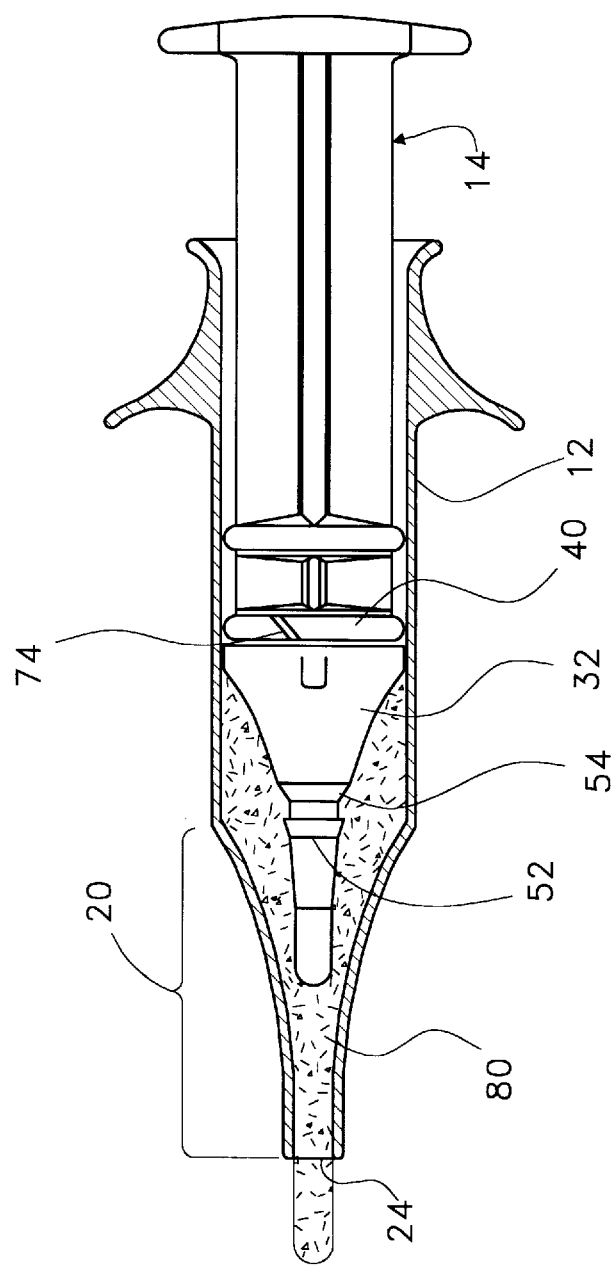
FIG. 5 is a side view of the syringe device shown in FIG. 1 at a point in time where the material in the syringe barrel is dispensed by an advancing piston assembly.

Referring to FIG. 5, it can be seen that as the displacement head 32 of the piston assembly 14 advances into the tapered region 20 of the syringe barrel 12, the high viscosity material 80 is becomes compressed in between the sloped surfaces of the displacement head 32 and the sloped interior of the tapered region 20 of the syringe barrel 12. The compression of the high viscosity material 80 is further advanced by the secondary deflection flanges 52, 54 that act to drive the high viscosity material 80 in the directions of the shown arrows, up against the sloping interior of the syringe barrel 12. The compression of the high viscosity material 80 acts to stress the material and squeeze the air pockets out of the high viscosity material 80 prior to that material exiting the dispensing port 24 at the end of the syringe barrel 12. The escaping air exits the syringe barrel 12 through the gap 74 in the forward O-ring 40 as has been previously described. The material 80 eventually displaced out of the dispensing port 24 at the front of the syringe device 10 is therefore relatively devoid of air pockets. The high viscosity material 80 can therefore be used for creating impressions, wherein the impression will contain far less defects due to air pocket voids.

It will be understood that the embodiment of the present invention described and illustrated herein is merely exemplary and a person skilled in the art can make many variations to the embodiment shown without departing from the scope of the present invention. All such variations, modifications and alternate embodiments are intended to be included within the scope of the present invention as defined by the appended claims.

What is claimed is:

1. A syringe device for dispensing a material, comprising:
   a hollow syringe barrel having an open first end and an open second end;
   a piston assembly positionable within said hollow syringe barrel, said piston assembly being capable of reciprocal movement within said hollow syringe barrel between a fully advanced position and a fully retracted position, said piston assembly including a first O-ring having an air pervious gap disposed therein, wherein said piston assembly contacts said hollow syringe barrel and forms a seal against said hollow syringe barrel that is substantially impervious to the material but is not impervious to the flow of air.

2. The device according to claim 1, wherein said piston assembly includes a second O-ring that produces at least part of said seal against said hollow syringe barrel.

3. The device according to claim 2, wherein said piston assembly defines at least one aperture under said second O-ring through which air can pass.

4. The device according to claim 1, wherein said hollow syringe barrel has a tapered region proximate said first end and said piston assembly includes a displacement head that extends into said tapered region when said piston assembly is in said fully advanced position.

5. The device according to claim 4, wherein said tapered region of said hollow syringe barrel defines a space of a predetermined shape and said displacement head has a shape that generally corresponds to said predetermined shape.

6. The device according to claim 4, further including at least one deflection flange on said displacement head that directs the material against the tapered region of said hollow syringe barrel as said piston assembly is moved toward said advanced position.

7. The device according to claim 1, wherein said piston assembly includes;
   a second O-ring for creating at least part of said seal against said hollow syringe barrel; and
   a baffle chamber disposed in between said first O-ring and said second O-ring, whereby air passing said first O-ring enters said baffle chamber prior to passing said second O-ring.

8. The device according to claim 1, wherein the piston assembly includes at least one stop element for preventing said piston assembly from being advanced in said syringe barrel beyond said advanced position.

9. A syringe device for dispensing a material, comprising:
   a syringe barrel having a first open end and an opposite second open end;
   a ramrod sized to fit within said syringe barrel;
   a piston head coupled to said ramrod within said syringe barrel, said piston head including a cut O-ring that defines a gap, wherein said gap is sized to inhibit the flow of the material but not of air and said piston head forms a seal against said syringe barrel that is substantially impervious to the material but is not substantially impervious to the flow of air.

10. The device according to claim 9, wherein said piston head includes two concentric circular flanges separated by a chamber.

11. The device according to claim 10, wherein each of said circular flanges has a groove disposed along its peripheral edge that is sized to retain an O-ring.

12. The device according to claim 11 wherein a first of said circular flanges is solid and a second of said circular flanges has at least one aperture formed therethrough.

13. The device according to claim 12, wherein said cut O-ring is set in said groove around said first circular flange and a continuous O-ring is set in said groove around said second circular flange.

14. A The device according to claim 9 wherein said piston head includes a displacement device that generally conforms to said syringe barrel in a region proximate said second end of said syringe barrel.

* * * * *